United States Patent [19]

Anaise et al.

[11] Patent Number: 5,110,721

[45] Date of Patent: May 5, 1992

[54] METHOD FOR HYPOTHERMIC ORGAN PROTECTION DURING ORGAN RETRIEVAL

[75] Inventors: David Anaise, Dix Hills; Marc Yland, Stony Brook, both of N.Y.

[73] Assignee: The Research Foundation of State University of New York, Albany, N.Y.

[21] Appl. No.: 309,288

[22] Filed: Feb. 10, 1989

[51] Int. Cl.$^5$ .............................................. A01N 1/02
[52] U.S. Cl. ...................................... 435/1; 435/283; 435/284; 435/287
[58] Field of Search ......................... 435/1, 283–287, 435/288, 289, 290; 62/306; 604/78

[56] References Cited

U.S. PATENT DOCUMENTS

| | | | |
|---|---|---|---|
| 3,406,531 | 10/1968 | Swenson et al. | 435/283 |
| 3,490,438 | 1/1970 | Lavender et al. | 128/1 |
| 3,545,221 | 12/1970 | Swenson et al. | 435/1 |
| 3,632,473 | 1/1972 | Belzer et al. | 435/1 |
| 3,660,241 | 5/1972 | Michielsen | 199/127 |
| 3,753,865 | 8/1973 | Belzer et al. | 435/283 |
| 3,995,444 | 12/1976 | Clark et al. | 62/306 |
| 4,186,565 | 5/1978 | Toledo-Pereyra | 62/306 |
| 4,192,302 | 3/1980 | Boddie | 128/400 |
| 4,416,280 | 11/1983 | Carpenter et al. | 128/399 |
| 4,427,009 | 1/1984 | Wells et al. | 128/400 |
| 4,473,637 | 9/1984 | Guibert | 435/1 |
| 4,476,867 | 10/1984 | Parks | 128/400 |
| 4,666,425 | 5/1987 | Fleming | 604/4 |
| 4,762,794 | 5/1988 | Nees | 435/284 |
| 4,837,390 | 6/1989 | Reneau | 435/1 |

OTHER PUBLICATIONS

Das,. Journal of Urology, vol. 121, Mar. 1979, pp. 262–264.
Webster's New World Dictionary, 3rd College Edition, p. 1481.
*Perfusion Nephropathy in Human Transplants*, the New England Journal of Medicine, vol. 295, No. 22, Nov. 25, 1976, pp. 1217–1221.
*Structural Injury Produced by Pulsatile Perfusion vs. Cold Storage Renal Preservation*, in Surgical Forum, undated, pp. 313–315.
*Preservation of Canine Kidneys*, published in Arch. Surg./vol. 98, Jan. 1969, pp. 121–127.
*The Usefulness of Initial Brief Pulsatile Perfusion in Extending the Applicability of Cold Storage for Renal Transplantation—A Preliminary Report*, published in Transplantation Proceedings, No. 4, Oct. 1988.
*A Small Perfusion Apparatus for the Study of Surviving Isolated Organs*, by Long and Lyons, Journal of Laboratory and Clinical Medicine, vol. 44, No. 4, Oct. 1954, pp. 614–626.
*A Pulsating Perfusion Apparatus*, by J. S. Long, dated 1947.
*A Simple Device to Obtain a Pulsatile Flow*, by Kachelhoffer et al., Eur. Surg. Res., 8:461–470 (1976).

(List continued on next page.)

*Primary Examiner*—Douglas W. Robinson
*Assistant Examiner*—Jane A. Williams
*Attorney, Agent, or Firm*—Hoffmann & Baron

[57] ABSTRACT

A device for maintaining, in situ, the viability of an organ of a non-heart beating cadaver includes a container for receiving a supply of solution, and a submersible pump contained in the container. An inflow catheter is partially inserted into the abdominal cavity of the cadaver. A first conduit is connected between the pump and the inflow catheter. A return catheter is inserted at least partially into the abdominal cavity. A second conduit is provided between the container and the return catheter. Solution is suctioned from the abdominal cavity by a third conduit connected to the pump and the second conduit and a venturi-type device connected in series with the third conduit and situated in proximity to the point at which the third conduit is connected to the second conduit. The third conduit provides solution to the venturi-device, which causes solution in the cavity to be drawn into the return catheter and the second conduit and to be returned to the container.

1 Claim, 2 Drawing Sheets

OTHER PUBLICATIONS

*Rapid In Vivo Multiple Organ Cooling Prior to Harvesting*, by Toledo-Pereyra, published in The American Surgeon, vol. 50:493-495 (1984).

*Effects of Perfusion Pressure During Flushing on the Viability of the Procured Liver Using Non Invasive Fluorometry*, by Tokunaga, et al., published in Transplantation, vol. 45, 1031-1035, No. 6, Jun. 1988.

*To Pulse or Not to Pulse*, by Mavroudis, published in the Annals of Thoracic Surgery, vol. 25, No. 3, pp. 259-271, Mar. 1978.

*Effect of Hypothermic Kidney Preservation on the Isolated Perfused Kidney: A Comparison of Reperfusion Methods*, by Rice et al., published in Cryobiology, vol. 22, pp. 161-167 (1988).

*Studies in Cryoprotection*, by Collins et al., published in Cryobiology, vol. 21, pp. 1-5 (1984).

METHOD FOR HYPOTHERMIC ORGAN PROTECTION DURING ORGAN RETRIEVAL

BACKGROUND OF THE INVENTION

1. Field of the Invention

This invention relates to a method and apparatus for donor organ preservation, and more particularly relates to a method and apparatus for in situ hypothermic organ protection during organ retrieval.

The science of organ preservation has been rapidly increasing in importance over recent years because of the increase in organ transplantation as a medical procedure. Basically, in organ preservation, an organ such as a kidney, liver, lung or heart is removed from a donor and maintained in viable condition by artificial means. This is done to maintain the organ until the recipient is selected and prepared to receive it.

At the present time, organs of potential donors have often been unavailable to recipients in desperate need of them because of limitation of current procurement techniques.

More specifically, current procurement technology allows the removal of organs from brain-dead trauma victims, that is, heart-beating donors who are otherwise in good physiological state. A large but yet untapped source of transplantable organs is victims of motor vehicle accidents who succumb to their injuries in the emergency room or in the intensive care unit, in other words, non-heart beating donors. Utilization of organs removed from these donor sources is limited, however. The usual legal requirement for obtaining consent from the families of the potential donor prior to retrieval of such organs and the need to secure an operating room result in a delay of at least 4 hours. This delay may cause injury to the organ targeted for removal due to the effects of warm ischemia. In the case of a kidney, for example, the maximum tolerance of kidney-to-warm ischemia is only about ½ hour.

Accordingly, in order to procure organs from non-heart beating cadaver sources, the following conditions should be met 1) rapid exclusion of the organ, such as the kidney, from the vascular tree; 2) rapid flush of the organ's microvasculature, resulting in rapid cooling of the organs, for example, to less than 15° C. in the case of a kidney, and removal of red blood cells from the microcirculation; and 3) maintenance of cold temperature of the organ for a given period of time, for example, for 4–5 hours in the case of a kidney.

All of these procedures must be performed with minimal violation of the body, that is, with no major abdominal or chest incision, prior to obtaining familial consent.

2. Description of the Prior Art

There exist a number of patents and publications which disclose a method or apparatus for organ preservation. For example, U.S. Pat. No. 4,666,425 (Fleming) discloses a device for perfusing an animal head. The purpose of the perfusing device disclosed in the Fleming patent is stated as being to keep a discorped head (i.e., severed from its body) alive or viable for ultimate transplantation.

FIG. 2 of the Fleming patent illustrates a severed head connected to process equipment and to a brain-dead body through the use of cannulae. The patent states that the main arteries and veins of the head are coupled to the arteries and veins of the neck of the body to complete the circuit. It is stated that the brain-dead body may be kept alive by artificial means so that the organs of the body, such as the kidneys, etc., perform their natural function in treating and oxygenating the blood passing through the discorped head.

Alternatively, and as illustrated by FIG. 3 of the Fleming patent, it is described in the patent that the discorped head may be kept alive by a pumping and treatment circuit, whose terminal ends are connected to the main arteries and veins of the head. It is further stated that the treatment circuit may include pumps 52 and 54 to drive blood in the circuit through the head, and a treatment chamber 56 which may, for example, introduce heparin to the blood to prevent clotting or which may heat or cool the blood in order to raise or lower the solubility of desired or undesired components. The patent describes the circuit as also including an oxygenation chamber 58 to add oxygen to the blood, and a waste removal chamber 60 to remove waste products.

It should be noted, however, that the method disclosed in the Fleming patent relates to keeping an organ (the head) alive, which organ is separated from the body. Accordingly, such a method would be inappropriate where unnecessary mutilation of the body prior to obtaining the consent of the potential donor's next of kin is to be avoided. Such disclosed method is also not performed in situ.

Other patents and publications disclose methods and devices for organ preservation. For example, U.S. Pat. No. 3,995,444 (Clark, et al.) discloses an organ perfusion system, in which it is described that an organ 21 removed from the body is placed into a chamber and connected to a conduit which provides a cold perfusion solution to the organ. The Clark, et al. patent states that the solution draining from the organ collects in a well and is removed through another conduit which passes through an ice bath to effect rapid cooling of the solution, and that the conduits are connected to an oxygenator 12, a pulsating pump 11 and a bubble trap 30, and returned to the organ to effect further cooling of the organ.

It should be noted that the organ has already been removed from the body in accordance with the method disclosed in the Clark, et al. patent, and thus the Clark, et al. patent does not address the problem associated with maintaining the viability of the organs in situ without a major invasion of the body prior to obtaining consent for the removal of the targeted organ.

Also, U.S. Pat. No. 3,660,241 (Michielson) discloses a container for transporting a transplant organ, where the container has a number of apertures through which pass conduits connected to the organ for providing a perfusion solution to the organ. The Michielson patent further states that the container may be filled with a solution to bathe the outside of the organ. Of course, the method and apparatus disclosed in the Michielson patent is for maintaining the viability of the organ after it is removed from the donor and not before.

An article, *A Small Perfusion Apparatus for the Study of Surviving Isolated Organs*, by Long & Lyons, shows, in FIG. 2B of the article, a diagrammatic representation of a perfusion circuit in which an organ, removed from the donor, is placed in a chamber and connected to a circuit to allow a perfusion solution to pass through it. The article does not disclose a method or apparatus which allows the targeted organ to be cooled in situ.

Also of interest is U.S. Pat. No. 4,192,302 (Boddie). The Boddie patent discloses a perfusion circuit which, through a plurality of shunts, allows blood circulation from the lower part of a patient's body and from the intestines to flow to the heart, while allegedly isolating hepatic venous blood containing toxic agents from the body's general circulation and returning it to a heart-lung machine. It is stated that circuit may be used to perfuse the liver of a patient which has become involved with cancer with extremely high doses of chemotherapy agents while at the same time avoiding the toxic effects of these agents on the patient's body as a whole.

The perfusion circuit disclosed in the Boddie patent is shown in FIG. 3 of the patent. The circuit requires a number of catheters for redirecting the patient's blood, and a number of ligatures (such as T1–T6) to hold the catheters in place and to occlude blood flowing into the liver from the hepatic artery.

It is to be noted that the Boddie patent does not disclose a minor invasion of the patient's body, as the perfusion circuit disclosed in the Boddie patent appears to require major surgery, nor does it describe a system or method for preserving organs of a potential donor for transplantation.

OBJECTS AND SUMMARY OF THE INVENTION

It is an object of the present invention to provide a method and apparatus for maintaining the viable state of an organ in situ.

It is another object of the present invention to provide a method and apparatus for maintaining the viability of an organ of a non-heart beating cadaver without necessitating a major mutilation of the cadaver prior to obtaining consent for the removal of a targeted organ.

It is a further object of the present invention to provide a method and apparatus for maintaining the viability of an organ of a non-heart beating cadaver which involve minimal invasive procedures and which procedures may be implemented in a relatively short period of time to minimize any detrimental effects caused by warm ischemia.

It is yet another object of the present invention to provide apparatus which can maintain the viability of a targeted organ of a potential donor, which apparatus is relatively inexpensive to manufacture and simple to use, and which requires minimal set up and connect time.

It is yet a further object of the present invention to provide a method and apparatus for maintaining an organ or organs of a potential donor in a viable state, in situ, and during the time required to obtain consent for the retrieval of the organ, which apparatus and method overcome the disadvantages of known organ preservation methods and apparatuses.

In accordance with one form of the present invention, apparatus for maintaining, in situ, the viability of an organ of a non-heart beating cadaver includes a container for receiving and holding a supply of cooled saline solution. A pump, preferably submersible, is placed in the container. The pump has an outlet to discharge the saline solution. An inflow catheter is adapted to be at least partially received by the abdominal cavity of the cadaver, and forms a seal with the abdominal cavity wall to minimize leakage of the solution. A first conduit is connected between the pump outlet and the inflow catheter, and is used for supplying the saline solution from the container to the abdominal cavity of the cadaver.

The apparatus further includes a return catheter which is also at least partially inserted into the abdominal cavity of the cadaver. A second conduit is connected to the return catheter and to the container. The second conduit and the return catheter are provided for removing the solution from the abdominal cavity.

The apparatus also includes a component which causes saline solution to be suctioned from the abdominal cavity of the cadaver and returned to the container. This component is in communication with the return catheter and the second conduit and, in its preferred form, includes a third conduit connected to the pump discharge outlet and to the second conduit, and a venturi-type device connected in series with the third conduit and situated in proximity to the point at which the third conduit is connected to the second conduit. The venturi-type device causes saline solution in the abdominal cavity to be drawn into the return catheter and returned through the second conduit to the container so that a steady flow of saline solution is provided to the abdominal cavity.

The saline solution provided to the abdominal cavity of the container is in a cooled state. This is accomplished by providing an ice bath for the solution held in the container, or by providing a heat exchanger in thermal communication with the first conduit or the second conduit.

In accordance with the method of the present invention, cold saline solution is provided to the abdominal cavity of the cadaver using the apparatus described above. The cold saline solution will bathe the organs of the cadaver situated at the abdominal cavity region thus cooling the organs exteriorly of the organs and in situ. Only minor incisions need be made in the abdominal cavity of the non-heart beating potential donor, one incision being made for placement of the inflow catheter, and the other incision being made for placement of the return catheter. Saline solution, which may be cooled by ice in the container, is provided to the abdominal cavity through the first conduit and the inflow catheter. The solution is removed from the abdominal cavity and returned to the container through the return catheter and the second conduit. The solution is drawn into the return catheter by the venturi-type device and third conduit described previously, so that a constant flow of cooled solution is provided to the abdominal cavity to bathe the organs of the cadaver. In effect, the apparatus of the present invention defines with the abdominal cavity of the cadaver a closed circuit for circulating cold saline solution to the organs of the potential donor.

These and other objects, features, and advantages of this invention will be apparent from the following detailed description of illustrative embodiments thereof, which is to be read in connection with the accompanying drawings.

DETAILED DESCRIPTION OF THE PREFERRED EMBODIMENTS

Figure 1:
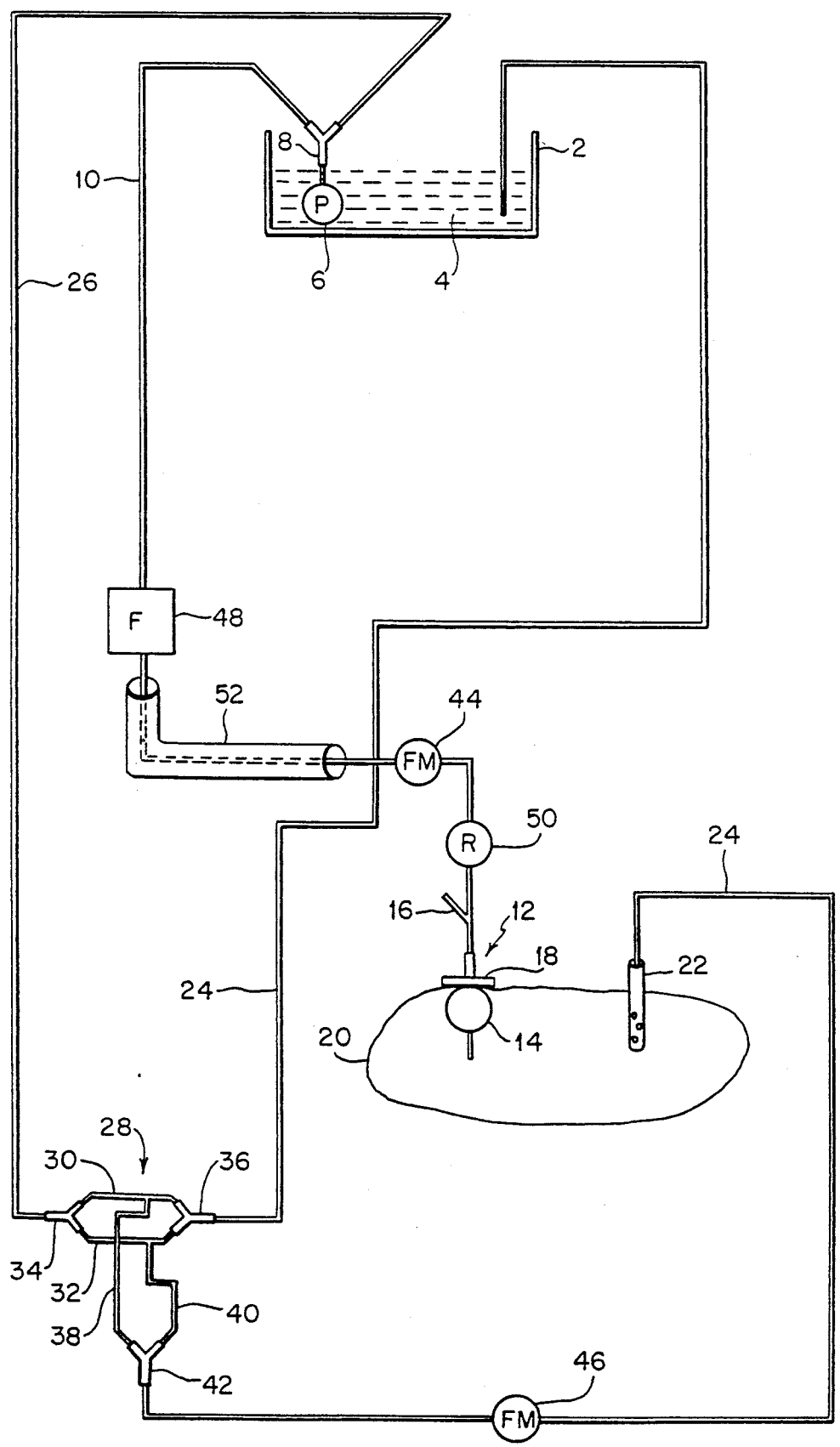
FIG. 1 is a pictorial illustration of one form of the apparatus of the present invention.

Referring initially to FIG. 1 of the drawings, it will be seen that an apparatus for maintaining, in situ, the viability of an organ of a non-heart beating cadaver, constructed in accordance with the present invention, includes a container 2 which is adapted to hold a solution 4, such as a saline solution, or the like. The solution 4 held by the container 2 may be chilled to a low temperature, such as 15° C., and more preferably to about 2°-4° C., as required to maintain the viability of the targeted organ undergoing treatment to ward off the effects of warm ischemia. Ice may be added to the container 2 to lower the temperature of the perfusion solution held by the container or, alternatively, the entire container may be subject to an ice bath contained in a second larger container (not shown). As will be described in connection with FIG. 2, a heat exchanger may also be employed to lower the temperature of the saline solution.

The apparatus further includes a pump 6 which is in fluid communication with the container and is, more preferably, placed in the container 2 and is submersible in the saline solution 4. An example of a pump 6 which may used is Model No. 2E-38N manufactured by the Little Giant Pump Company of Oklahoma City, Okla.

The pump 6 has an outlet for discharging saline solution 4 contained in the container 2 and drawn into the pump.

The pump outlet is connected to a Y connector 8. The Y connector 8 includes one inlet port which is connected to the pump outlet, and two outlets ports. One of the outlet ports is connected to a first conduit 10. The first conduit is basically flexible biomedical tubing which is used to carry the saline solution 4 pumped into it from the container 2.

The first conduit 10 is connected to an inflow catheter 12. The inflow catheter 12 is basically a balloon catheter having multiple side holes, and a balloon 14 proximal to the side holes and which inflates by blowing into an inflation port 16 provided on the catheter 12. A guard plate 18 is also provided on the catheter. A trocar inside the catheter allows for rapid insertion of the catheter. The inflow catheter is typically about 12 Fr in diameter. Although many different balloon catheters may be suitable for use, one in particular is the MIC gastrostomy tube manufactured by Medical Innovation Corporation located in Milpitas, Cal.

The inflow catheter 12 is inserted through a minor incision partially into the abdominal cavity 20 of the cadaver, that is, up to the guard plate 18, and located at just below either the xyphoid or the umbilicus. The balloon 14 of the inflow catheter 12 is then inflated such that it exerts pressure on the abdominal cavity wall, which wall is wedged between the balloon 14 and guard 18 of the catheter 12. This effects a substantially fluid-tight seal to minimize leakage of saline solution, which solution will be forced into the abdominal cavity 20 of the cadaver through inflow catheter 12, first conduit 10 and pump 6.

The apparatus further includes a return catheter 22. The return catheter 22 is partially inserted into the abdominal cavity 20 of the cadaver through a second minor incision made in the abdominal cavity wall and located at just below the other of the xyphoid and the umbilicus. The return catheter, which is typically 24 Fr in diameter, also has a plurality of side holes, and may be safely and easily introduced by using a trocar. Many catheters are suitable for use as the return catheter 22. For example, an MIC gastrostomy tube, manufactured by Medical Innovation Corporation, may be used as the return catheter.

The apparatus further includes a second conduit 24 which is generally connected between the return catheter 22 and the container 2 so that saline solution may be removed from the abdominal cavity 20 and returned to the container 2. Like the first conduit 10, the second conduit 24 is made of a flexible tubing, such as biomedical tubing.

The apparatus of the present invention is further provided with means for suctioning saline solution from the abdominal cavity of the cadaver. In the preferred form shown in FIG. 1, the solution suctioning means includes a third conduit 26 which is connected to the other output port of the Y connector 8 and to the second conduit 24, and a venturi-type device, designated generally by reference numeral 28, which is connected in series with the third conduit 26 and situated in proximity to the point at which the third conduit is connected to the second conduit 24. The venturi-type device basically includes two parallel segments 30, 32 joined together at corresponding axial ends by Y connectors 34, 36. The second conduit 24 is divided through a Y connector 42 into two connective branches 38, 40, which branches are connected to segments 30, 32 of the venturi-type device.

Saline solution 4 from container 2 is provided to the venturi-type device 28 by the third conduit 26. As its names applies, the venturi-type device 28 provides a constriction to the saline solution flowing through it so that the pressure of the saline solution decreases at a point in the second conduit 24 where the venturi-type device (and the third conduit 26) are joined to the second conduit 24. This produces a suction in the second conduit 24 and the return catheter 22 so that saline solution supplied to the abdominal cavity through the inflow catheter 12 and the first conduit 10 will be drawn into the return catheter 22 and returned to the container 2 through the second conduit 24. One suitable venturi-type device which may be used in the present invention is Model No. 6140 manufactured by Nalgene Company.

It may also be desirable to include a flow meter 44 in series with the first conduit 10, and a flow meter 46 in series with the second conduit 24 to monitor the flow of saline solution into and out of the abdominal cavity 20 of the cadaver. A typical flow meter which may be used for such purposes is Model No. H19937 manufactured by Bel Art Products. It may also be desirable to include a filter 48 in series with the first conduit 10. A 0.2 u filter will provide substantially complete filtering and sterilization of the system and thus sterile solution is not required. Also, filter 48 will allow non-sterile ice to be used for cooling the saline solution in container 2 while maintaining the sterility of the system. This is an advantageous feature because non-sterile ice is normally available in the operting room and, accordingly, may be quickly obtained and used in the apparatus. Thus, a physician or medical assistant will have everything he needs in the operating room to quickly set up the equipment and provide cold solution to the cadaver immediately upon death, which will minimize the detrimental effects of warm ischemia. A typical filter 48 which may be used is a Pre By-Pass Plus filter, Model No. PP3802, manufactured by Pall Corporation of New York.

It may also be desirable to include a restrictor 50 in series with the first conduit 10. The restrictor 50 is used to help control the flow of saline solution into the abdominal cavity 20 of the cadaver. The restrictor 50 may be adjusted so that the abdominal cavity 20 is always maintained in an inflated state such that an ample supply of solution is contained in the cavity and bathes the organs in the abdominal cavity targeted for removal and transplantation. A typical restrictor 50 which may be used is Model No. 2C4030 manufactured by Baxter Travenol Laboratories, Inc.

It is also desirable to maintain the saline solution supplied to the abdominal cavity 20 at a low temperature. This can be further accomplished by using an outer insulating tube 52 which surrounds the first conduit 10 over at least a portion of its length. The outer insulating tube 52 may include an insulating material between it and the first conduit 10, such as styrofoam or the like, to minimize any increase in temperature of the perfusion solution as it travels from the container 2 through the first conduit 10 to the abdominal cavity 20.

Figure 2:
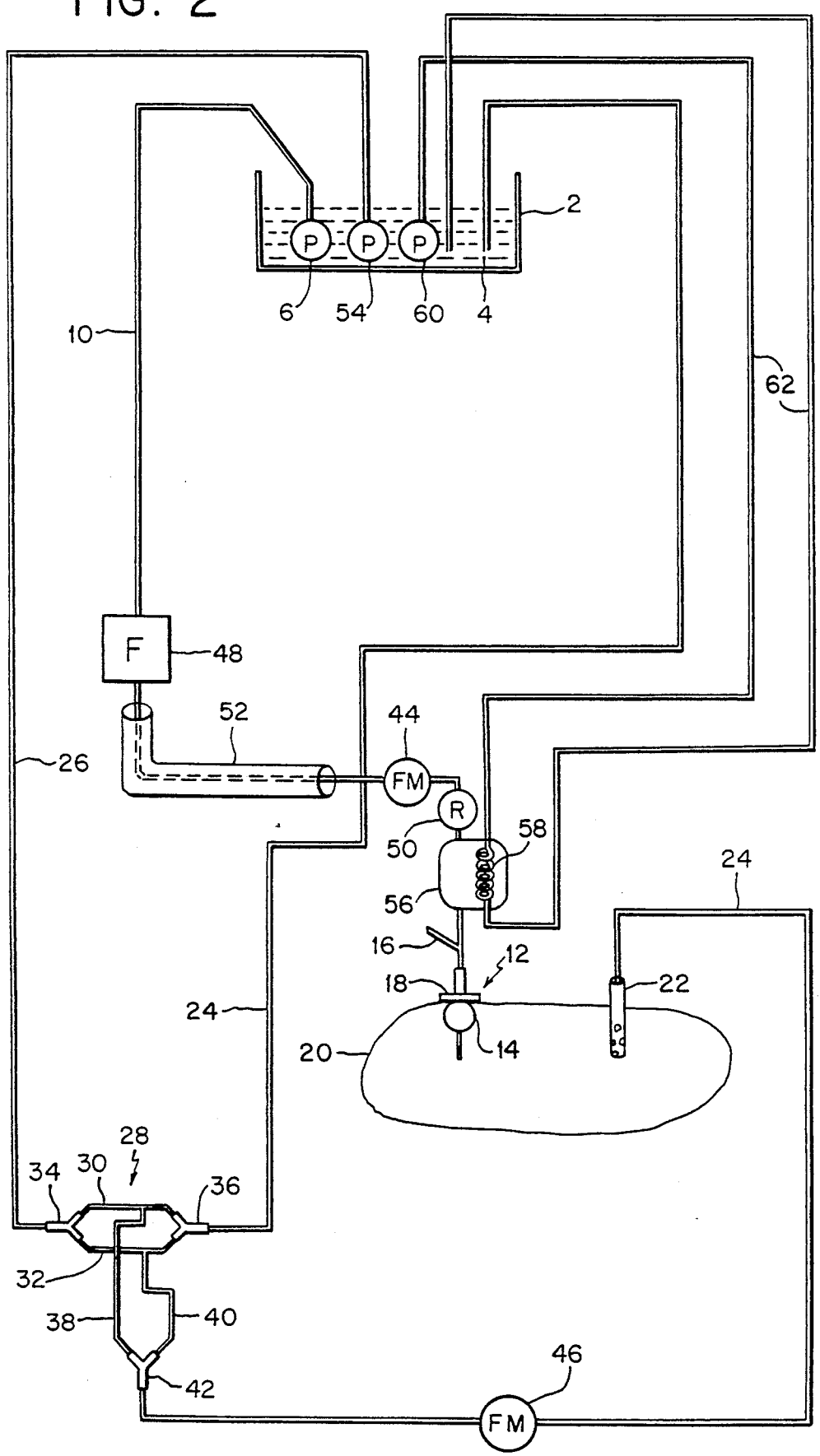
FIG. 2 is a pictorial illustration of a second form of the apparatus of the present invention.

An alternative embodiment of the apparatus of the present invention is illustrated by FIG. 2 of the drawings. In FIG. 2 it is shown that a second pump 54, also submersible, may be employed as part of the solution suctioning means. The second pump 54 is connected to the third conduit 26, as opposed to the third conduit being connected to the second outlet port of the Y connector 8 (which in the second embodiment may be eliminated) and to the first pump 6. The use of a second pump 54 in this alternative embodiment provides more freedom in selecting the flow rate into the venturi-type device 28 to create the desired drop in pressure needed to suction solution out of the abdominal cavity 20 and into the return catheter 22 and second conduit 24.

In addition, in the second embodiment illustrated by FIG. 2, the outer insulating tube 52 of the first embodiment may be eliminated or may be supplemented by a heat exchanger 56 connected generally in series with the first conduit 10 (or, if desired, the second conduit 24). Basically, the heat exchanger 56 includes a cooling coil in thermal communication with the first conduit 10. The cooling coil may be connected to a separate pump 60 or one of the the other two pumps 6, 54 described previously, through a fourth conduit 62 in fluid communication with container 2, which allows a faster flow of low temperature solution to pass through the cooling coil and to be returned to the container 2. Since the solution flows at a faster rate through the cooling coil 58 than the solution flowing through the first conduit 10, the solution through the cooling coil will not heat up significantly, and may be used to lower the temperature of the solution flowing through the first conduit prior to its passage into the abdominal cavity 20 of the cadaver. Alternatively, the cooling coil 58 of the heat exchanger may be connected to a different source of cooling fluid other than the solution contained in container 2. A typical heat exchanger 56 which may be used is Model No. 2720 manufactured by Dideco Co.

As can be seen from FIGS. 1 and 2 of the drawings, the method of the present invention basically allows cooling of the organ in situ using the prospective donor's abdominal cavity as a container for receiving and holding the cold saline solution. The pump 6 forces the solution into the cavity through the inflow catheter 12, and a return circuit continuously suctions the solution out of the cavity for re-cooling and recirculation. Accordingly, the apparatus of the present invention, in combination with the abdominal cavity 20 of the cadaver, defines a closed loop circuit for circulating cooled saline solution, which solution bathes the organs of the cadaver located in the abdominal region. Only a minor incision need be made in the cadaver for insertion of the inflow and return catheters 12, 22.

Accordingly, the method of the present invention includes the steps of providing cooled solution to the abdominal cavity of a cadaver by pumping such solution from the container 2 through the first conduit 10 and through the inflow catheter 12, which forms a substantially fluidtight seal with the abdominal wall of the cadaver, creating a venturi-effect to cause solution contained in the abdominal cavity to be suctioned out of the cavity, which effect may be provided by having a third conduit 26 connected to a venturi-type device 28, and withdrawing solution from the abdominal cavity 20 through a return catheter 22 and second conduit 24 back to the container 2 holding a supply of solution, the third conduit 26 being connected to the second conduit 24, and the venturi-type device 28 being connected in series with the third conduit 26 and located in proximity to the point at which the third conduit 26 is connected to the second conduit 24.

Filtering the saline solution in conduit 10 may be provided by filter 48, monitoring the flow of solution in conduit 10 and conduit 24 may be accomplished by using flow meters 44 and 46, respectively, and controlling the flow of solution into the abdominal cavity 20 may be accomplished by using the restrictor 50, all of which were described previously in relation to FIGS. 1 and 2 of the drawings. Furthermore, the cool temperature of the solution may be maintained by using the insulating tube 52 described previously, or the heat exchanger 56 illustrated by FIG. 2.

The present invention may be used in conjunction with the in situ flush cooling method performed by insertion of the Anaise organ procurement cannula into the femoral vessel of the donor, as described in U.S. Pat. No. 4,723,939. Peritoneal cooling can thus be used in conjunction with continuous hypothermic perfusion or in conjunction with a brief flush of the organs followed by cold storage until removal of the organs is feasible. This latter technique offers the advantage of greater simplicity and thus can be readily implemented by health professionals such as trained medical technicians, rather than by surgeons.

The apparatus of the present invention may be provided as a kit which includes disposal surgeons gowns, gloves, drapes, etc., all of which can be packaged in a plastic container that can be used as the container 2 for holding the perfusion solution ice bath. The kit may be assembled in minutes, and the catheters 12, 22 may be inserted into the peritoneal or abdominal cavity by a technician or resident within minutes after declaration of death, and thus will arrest the ischemic process while the more delicate and time consuming insertion of the Anaise cannula in the femoral vessel is performed, in accordance with the method described in U.S. Pat. No. 4,723,939.

Very little equipment is required in the apparatus of the present invention, and such components are readily available and quite inexpensive, so that a hospital may have several such kits on hand in emergency areas and operating rooms. The apparatus is also quite compact, requiring very little storage space. The container 2 may be placed on the floor of the emergency or operating room so that gravity will assist the flow solution from the cadaver back to the container.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A method for maintaining, in situ, the viability of an organ of a non-heart beating cadaver, which comprises the steps of:

providing cooled solution to a cavity of a cadaver through an inflow catheter inserted at least partially into the cavity of the cadaver, the solution being contained in a container and being provided to the cavity of the cadaver by a pump in fluid communication with the container and a first conduit communicating with the pump and the inflow catheter; and removing solution at a predetermined rate from the cavity of the cadaver for recirculation and recooling, the solution being removed from the cavity by a return catheter inserted at least partially into the cavity, and a second conduit communicating with the container and the return catheter, whereby the container, pump, inflow catheter, first conduit, return catheter and second conduit define, with the cavity of the cadaver, a closed fluid circuit for continually providing cooled solution to the cavity and for removing solution therefrom.

* * * * *